US009603927B2

(12) United States Patent
Doshi

(10) Patent No.: US 9,603,927 B2
(45) Date of Patent: *Mar. 28, 2017

(54) COMBINATION THERAPIES WITH ANTI-CD38 ANTIBODIES

(71) Applicant: Janssen Biotech, Inc., Horsham, PA (US)

(72) Inventor: Parul Doshi, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/629,941

(22) Filed: Feb. 24, 2015

(65) Prior Publication Data

US 2015/0246123 A1 Sep. 3, 2015

Related U.S. Application Data

(60) Provisional application No. 61/946,002, filed on Feb. 28, 2014, provisional application No. 62/006,386, filed on Jun. 2, 2014.

(51) Int. Cl.
| A61K 39/395 | (2006.01) |
| A61K 31/675 | (2006.01) |
| A61K 31/65 | (2006.01) |
| A61K 31/4745 | (2006.01) |
| A61K 31/573 | (2006.01) |
| A61K 31/00 | (2006.01) |

(52) U.S. Cl.
CPC ........ *A61K 39/39558* (2013.01); *A61K 31/00* (2013.01); *A61K 31/4745* (2013.01); *A61K 31/573* (2013.01); *A61K 31/65* (2013.01); *A61K 31/675* (2013.01)

(58) Field of Classification Search
None
See application file for complete search history.

(56) References Cited

U.S. PATENT DOCUMENTS

| 6,737,056 | B1 * | 5/2004 | Presta | C07K 16/4291 |
| | | | | 424/133.1 |
| 7,829,673 | B2 * | 11/2010 | De Weers | C07K 14/70596 |
| | | | | 424/130.1 |
| 7,829,693 | B2 | 11/2010 | Kreutzer et al. | |
| 8,088,896 | B2 | 1/2012 | Tesar et al. | |
| 9,040,050 | B2 * | 5/2015 | Van De Winkel | A61K 39/39558 |
| | | | | 424/141.1 |
| 2007/0148178 | A1 | 6/2007 | Fyfe et al. | |
| 2009/0076249 | A1 | 3/2009 | Deweers et al. | |
| 2009/0148449 | A1 * | 6/2009 | De Weers | C07K 14/70596 |
| | | | | 424/135.1 |
| 2009/0304687 | A1 * | 12/2009 | Drachman | A61K 39/39533 |
| | | | | 424/133.1 |
| 2010/0068136 | A1 * | 3/2010 | Hansen | A61K 51/1027 |
| | | | | 424/1.49 |
| 2011/0293606 | A1 * | 12/2011 | Lejeune | A61K 31/00 |
| | | | | 424/133.1 |
| 2011/0300157 | A1 | 12/2011 | Devy et al. | |
| 2012/0201827 | A1 * | 8/2012 | Elias | C07K 16/2896 |
| | | | | 424/139.1 |
| 2012/0231008 | A1 | 9/2012 | Guo et al. | |
| 2013/0109593 | A1 | 5/2013 | Hartmann et al. | |
| 2015/0231235 | A1 * | 8/2015 | Van De Winkel | A61K 39/3955 |
| | | | | 424/139.1 |

FOREIGN PATENT DOCUMENTS

| EP | 2567976 | 3/2013 |
| WO | WO 89/08114 | 9/1989 |
| WO | WO 92/01049 | 1/1992 |
| WO | WO 94/17184 | 8/1994 |
| WO | WO 96/16990 | 6/1996 |
| WO | WO 98/16245 | 4/1998 |
| WO | WO 98/16254 | 4/1998 |
| WO | WO 98/50435 | 11/1998 |
| WO | WO 99/62526 | 12/1999 |
| WO | WO 00/06194 | 2/2000 |
| WO | WO 00/40265 | 7/2000 |
| WO | WO 02/06347 | 1/2002 |
| WO | WO 02/32288 | 4/2002 |
| WO | WO 2004/058288 | 7/2004 |
| WO | WO 2005/042019 | 2/2005 |
| WO | WO 2005/044855 | 5/2005 |
| WO | WO 2005/103083 | 11/2005 |
| WO | WO 2006/088951 | 8/2006 |
| WO | WO 2006/099875 | 9/2006 |
| WO | WO 2006/125640 | 11/2006 |
| WO | WO 2007/042309 | 4/2007 |
| WO | WO 2008/047242 | 4/2008 |
| WO | WO 2008/150530 | 12/2008 |
| WO | WO 2011/154453 | 12/2011 |
| WO | WO 2012/092612 | 7/2012 |

OTHER PUBLICATIONS

George et al. (Circulation. 1998; 97: 900-906.*
Brown et al (J. Immunol. May 1996; 156(9):3285-3291.*
Vajdos et al (J. Mol. Biol. Jul. 5, 2002;320(2); 415-428).*
Aarhust, et al., "ADP-ribosyl Cyclase and CD38 Catalyze the Synthesis of a Calcium mobilizing Metabolite from NADP+," the Journal of Biological Chemistry, 270(51):30327-30333 (1995).
Armitage, et al., "Long-Term Remission Durability and Functional Status of Patients.Treated for Diffuse Histiocytic Lymphoma With the CHOP Regimen," Journal of.Clinical Oncology, 2(8): 898-902 (1984).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Chou, et al., "Drug Combination Studies and their Synergy Quantification Using the Chou-Talalay Method," Cancer Research, 70(2): 440-446 (2010).
P.M. Colman, "Effects of amino acid sequence changes on antibody-antigen.interactions, A Structural View of Immune Recognition by Antibodies," Biomolecular Research Institute, 33-36. (1994).

(Continued)

*Primary Examiner* — Sheela J Huff
(74) *Attorney, Agent, or Firm* — Kirk Baumiester

(57) ABSTRACT

The present invention relates to combination therapies with anti-CD38 antibodies.

18 Claims, 6 Drawing Sheets

(56) References Cited

OTHER PUBLICATIONS

Cotner, et al., "Human T Cell Proteins Recognized by Rabbit Heteroantisera and Monoclonal Antibodies," International Journal of Immunopharmaceuticals, 3(3): 255-.268 (1981).
Davies, et al., "Affinity improvement of single antibody VH domains: residues in all three hypervariable regions affect antigen binding," Immunotechnology, 2: 169-179 (1996).
Davis, et al., "Transgenic mice as a source of fully human antibodies for the treatment of cancer," Cancer and Metastasis Reviews, 18: 421-425 (1999).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," the Journal of Immunology, 169: 3076-3084 (2002).
Carina Dennis, "Off by a Whisker," Nature, 442 (17): 749-741 (2006).
Ellis, et al., "Engineered Anti-CD38 Monoclonal Antibodies for Immunotherapy of Multiple Myeloma," the Journal of Immunology, 155: 925-937 (1995).
Engert, et al., "A Phase-I Study of an Anti-CD25 Ricin A-Chain Immunotoxin (RFT5-SMPT-dgA) in Patients with Refractory Hodgkin's Lymphoma," Blood, 99(2): 403-410 (1997).
Ferrero, et al., Characterization and phylogenetic epitope mapping of CD38 ADPR cyclase in the cynomolgus macaque, BMC Immunology, 5(21): 1-13 (2004).
Field-Smith, "Bortezomid (VelcadeTM) in the treatment of multiple myeloma," Therapeutic and Clinical Risk Management, 2(3): 271-279 (2006).
Franco, et al., "The transmembrane glycoprotein CD38 is a catalytically active transporter responsible for generation and influx of the second messenger cyclic Adp-ribose across membranes," Faseb Journal, 12: 1507-1520 (1998).
Fujimori, et al., "A Modeling Analysis of Monoclonal Antibody Percolation Though Tumors: a Binding-Site Barrier," Journal of Nucleic Medicine, 31: 119-1198 (1990).
Funaro et al., "CD38 Functions Are Regulated Through an Internalization Step," Journal of Immunology, 160: 2238-2247 (1998).
Funaro, et al., "Human CD38: a versatile leukocyte molecule with emerging clinical prospectives," Fundamental and Clinical Immunology, 3(3): 101-113 (1995).
Funaro, et al., "Identification and characterization of an active soluble form of human CD38 in normal and pathological fluids," International Immunology, 8(11): 16431650 (1998).
Funaro, et al., "Involvement of the Multilineage CD38 Molecule in a Unique Pathway of Cell Activation and Proliferation," the Journal of Immunology, 145: 2390-2396 (1990).
Gallo, et al., "The human immunoglobulin loci introduced into mice: V(D) and J gene segment usage similar to that of adult humans," European Journal of Immunology, 30: 534-540 (2000).
"Humanx-CD38 Effective in Preclinical Studies," Genmab a/S, Stock Exchange Release 57/2005. ( 2005 ).
Goldmacher, et al., "Anti-CD38-Blocked Ricin: an immunotoxin for the Treatment of Multiple Myeloma," the American Society of Hematology, 84(9): 3017-3025 (1994).
Graeff, et al., "Enzymatic Synthesis and Characterizations of Cyclic GDp-ribose," the Journal of Biological Chemistry, 269(48): 30260-30267 (1994).
Green, et al., "Antigen-specific human monoclonal antibodies from mice engineered with hyman Ig heavy and light chain YACs," Nature Genetics, 7: 13-21 (1994).
Larry L. Green, "Antibody engineering via genetic engineering of the mouse: XenoMouse strains are a vehicle for the facile generation of therapeutic human monoclonal antibodies," Journal of Immunological Methods, 231: 11-23 (1999).
Guse et al., "Regulation of calcium signaling in T lymphocytes by the second messenger cyclic Adp-ribose," Nature 398:70-73, 1999.
Adriouch et al., "Extracellular Nad+: a danger signal hindering regulatory T cells," Microbes and Infection, 14:1284-1292 (2012).
Skeel, Handbook of Cancer Gliemotherapy, 3rd edition, Little, Brown & Co., pp. 343 (1991).
Moharhmad, et al., Gun. Cancer Res., 25: 4950 (2000).
Cheson et al., J Clin Oncology 25:579-586, 2007.
Terhorst, et al., "Biochemical Studies of the Human Thymocyte Cell-Surface Antigens T6, T9 and T10," Cell, 23: 771-780 (1981).
McKelvey et al., Cancer 1484-1493; 1976.
Armitage et al., "Long-Term Remission Durability and Functional Status of Patients Treated for Diffuse Histiocytic Lymphoma with the Chop Regimen," J. Clin. Oncol. 2:898-902, 1984.
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor a-expressing Lymphoma Utilizing the α-emitting Radionuclide-eonjugated Monoclonal Antibody 212Bi-anti-Tac, Cancer Research, 54: 4362-4370 (1994).
Henry, et al., "The use of basiliximab in solid organ transplantation," Expert Opinion Pharmacotherapy, 3(10: 1657-1663 (2002).
Holm, et al., "Functional mapping and single chain construction of the anti-cytokeratin 8 monoclonal antibody TS1," Molecular Immunology, 44: 1075-1084 (2002).
Hoshino, et al., "Mapping of the Catalylic and Epitopic Sites of Human CD38/NAD$^+$ Glycohydrolase to a Functional Domain in the Carboxyl Terminus[1]," the Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Jackson, et al., "Isolation of a cDNA Encoding the Human CD38 (T10) molecule, A Cell Surface Glycoprotein With an Unusual Discontinuous Pattern of Expression During Lymphocyte Differentiation," the Journal of Immunology, 144(7): 2811-2815 (1990).
Sundar Jagannath, Multiple Myeloma Update from the American Society of Clinical Oncology (ASCO) 41$^{st}$ Annual meeting. date not available.
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Aya Jakoboits, "The long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia. morphologic, immunophenotypic , and cytogenetic features of 4 cases treated with chemotherapy and stem cell transplantation," Annals of Diagnostic Pathology, 10: 263-268 (2006).
Jones, et al., "Replacing the complementarity-determining regions in a human antibody with those from a mouse," Nature, 321: 522-525 (1986).
Jones, et al., "Depletion of CD25+ regulatory calls results in suppression of melanoma growth and induction of autoreactivity in mice," Cancer Immunity, 2: 1 (2002). Abstract.
Konopleva, et al., "CD38 in Hematopoietic Malignancies," Chemical Immunol. Basel Karger, 75: 189-206 (2000).
Konapleva, et al., "Ligation of Cell Surface CD38 Protein with Agonistic Monoclonal Antibody Induced a Cell Growth Signal in Myeloid Leukemia Cells," the Journal of Immunology, 161: 4702-4708 (1998).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Kropff, et al., "Bortezomib in combination with dexamethoasone for relapsed multiple myeloma," Leukemia Research, 29: 587-590 (2005).

(56) References Cited

OTHER PUBLICATIONS

Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kupiec-Weglinski, "CD25-Targeted Therapy Revisited," Transplantation, 69(3): 38-330 (2000).
Lande, et al., "CD38 ligation plays a direct role in the induction of Il-113, 1-6, and Il-10 secretion in resting human monocytes," Cellular Immunology, 220: 30-38 (2002).
Laurie, et al., "The role of CD4+CD25+ immunoregulatory T cells in the induction of autoimmune gastritis," Immunology and Cell Biology, 89: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Lin, et al., "Structure-Function Relationships in Glucagon: Properties of Highly Purified DesHis1-, Monoiodi-, and [Des-Asn$^{28}$, Thr$^{29}$](homoserine lactone$^{27}$)-glucagon," Biochemistry, 14(9): 1559-1563 (1975).
Lonberg, et al., "Antigen-specific human antibodies from mice comprising four distinct genetic modifications," Nature: 308: 856-859 (1994).
MacCallum, et al., "Antibody-antigen Interactions: Contact Analysis and Binding Site Topography," Journal of Molecular Biology, 262, 732-745 (1998).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Morrison, et al., "Chimeric human antibody molecules: Mouse antigen-binding domains with human constant region domains," Proceedings of the National Academy of Science USA, 8 6851-6855 (1984).

Ulrich Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, et al., "Recognition of antigens by single-domain antibody fragments: the superfluous luxury of paired domains," Trends in Biochemical Sciences, 26(4): 230-235 (2001).
Serge Muyldermans, "Single domain camel antibodies: current status," Reviews in molecular Biotechnology, 74: 277-302 (2001).
Nikaido, et al., "Molecular cloning of cDNA encoding human interleukin-2 receptor," Nature, 311: 631-635 (1984)
Onizuka, et al., "Tumor Rejection by in Vivo Administration of Anti-CD25 (Interleukin-2 Receptor α Monoclonal Antibody," Cancer Research, 59: 328-3133 (1999).
Robert Z. Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Parren, et al., HuMax-CD38, Torino, Jun. 8-10, 2006).
Parren, et al., HuMax-CD38, Myconos, Jun. 26, 2006.
Pascual, et al., "Anti-interleukin-2 receptor antibodies: basiliximab and daclizumab," Nephrology Dial. Transplant, 16: 1756-1760 (2001).
William E Paul, M.D., "Fundamental Immunology," Chapter 9, Raven Press, New York, 3'1 ed., 29-295 (1993).
Peipp, et al., 47th Annual Meeting of the American Society of Hematology, Atlanta, Ga, Dec. 10-13 (2005). (Meeting Abstract).
Peng, et al., "Oncolytic measles viruses displaying a single-chain antibody against CD38, a myeloma cell marker," Blood, 101, 2557-2562 (2003).
Shubinsky, et al., "The CD38 Lymphocyte Differentiation Marker: New Insight into Its Ectoenzymatic Activity and Its Role as a Signal Transducer," Immunity, 7: 315-324 (1997).

* cited by examiner

SEQUENCE LISTING

<160> NUMBER OF SEQ ID NOS: 20

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile

```
            115                 120                 125
Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: 005 mAb VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120
```

<210> SEQ ID NO 5
<211> LENGTH: 107
<212> TYPE: PRT
<213> ORGANISM: Artificial Sequence
<220> FEATURE:
<223> OTHER INFORMATION: 005 mAb VL

<400> SEQUENCE: 5

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105
```

<210> SEQ ID NO 6
<211> LENGTH: 5
<212> TYPE: PRT
<213> ORGANISM: Artificial Sequence
<220> FEATURE:
<223> OTHER INFORMATION: 005 mAb HCDR1

<400> SEQUENCE: 6

```
Ser Phe Ala Met Ser
 1               5
```

<210> SEQ ID NO 7
<211> LENGTH: 17
<212> TYPE: PRT
<213> ORGANISM: Artificial Sequence
<220> FEATURE:
<223> OTHER INFORMATION: 005 mAb HCDR2

<400> SEQUENCE: 7

```
Ala Ile Ser Gly Ser Gly Gly Gly Thr Tyr Tyr Ala Asp Ser Val Lys
 1               5                  10                  15

Gly
```

<210> SEQ ID NO 8
<211> LENGTH: 13
<212> TYPE: PRT
<213> ORGANISM: Artificial Sequence
<220> FEATURE:
<223> OTHER INFORMATION: 005 mAb HCDR3

```
<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: 005 mAb LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: 005 mAb LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: 005 mAb LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: 005 mAb heavy chain

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: 005 mAb light chain

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
            35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 14
<211> LENGTH: 122
<212> TYPE: PRT
<213> ORGANISM: Artificial Sequence
<220> FEATURE:
<223> OTHER INFORMATION: 003 mAb VH

<400> SEQUENCE: 14

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Phe Ser Trp Val Arg Gln Ala Pro Gly Gln Gly Leu Glu Trp Met
             35                  40                  45

Gly Arg Val Ile Pro Phe Leu Gly Ile Ala Asn Ser Ala Gln Lys Phe
 50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Asp Ile Ala Ala Leu Gly Pro Phe Asp Tyr Trp Gly Gln
                100                 105                 110

Gly Thr Leu Val Thr Val Ser Ser Ala Ser
                115                 120

<210> SEQ ID NO 15
<211> LENGTH: 107
<212> TYPE: PRT
<213> ORGANISM: Artificial Sequence
<220> FEATURE:
<223> OTHER INFORMATION: 003 mAb VL

<400> SEQUENCE: 15
```

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
            85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: 024 mAb VH

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
            115                 120

<210> SEQ ID NO 17
<211> LENGTH: 107
<212> TYPE: PRT
<213> ORGANISM: Artificial Sequence
<220> FEATURE:
<223> OTHER INFORMATION: 024 mAb VL

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: MOR202 VH

<400> SEQUENCE: 18

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Tyr Met Asn Trp Val Arg Gln Ala Pro Gly Lys Gly Leu Glu Trp Val
             35                  40                  45

Ser Gly Ile Ser Gly Asp Pro Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 19
<211> LENGTH: 109
<212> TYPE: PRT
<213> ORGANISM: Artificial Sequence
<220> FEATURE:
<223> OTHER INFORMATION: MOR202 VL

<400> SEQUENCE: 19

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Arg His Tyr Tyr Val
                 20                  25                  30

Tyr Trp Tyr Gln Gln Lys Pro Gly Gln Ala Pro Val Leu Val Ile Tyr
             35                  40                  45

Gly Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
                 85                  90                  95

Val Phe Gly Gly Gly Thr Lys Leu Thr Val Leu Gly Gln
            100                 105

<210> SEQ ID NO 20
```

```
<211> LENGTH: 4
<212> TYPE: PRT
<213> ORGANISM: Homo sapiens

<400> SEQUENCE: 20

Val Gln Leu Thr
1
```

COMBINATION THERAPIES WITH ANTI-CD38 ANTIBODIES

CROSS-REFERENCE TO RELATED APPLICATIONS

This application claims the benefit of U.S. Provisional Application Ser. No. 61/946,002, filed 28 Feb. 2014 and U.S. Provisional Application Ser. No. 62/006,386, filed 2 Jun. 2014. The entire contents of each of the aforementioned applications is incorporated herein by reference in their entirety.

FIELD OF THE INVENTION

The present invention relates to combination therapies with anti-CD38 antibodies.

BACKGROUND OF THE INVENTION

CD38 is a multifunctional protein having function in receptor-mediated adhesion and signaling as well as mediating calcium mobilization via its ecto-enzymatic activity, catalyzing formation of cyclic ADP-ribose (cADPR) and ADPR. CD38 mediates cytokine secretion and activation and proliferation of lymphocytes (Funaro et al., J Immunolog 145:2390-6, 1990; Terhorst et al., Cell 771-80, 1981; Guse et al., Nature 398:70-3, 1999). CD38, via its NAD glycohydrolase activity, also regulates extracellular $NAD^+$ levels, which have been implicated in modulating the regulatory T-cell compartment (Adriouch et al., 14:1284-92, 2012; Chiarugi et al., Nature Reviews 12:741-52, 2012). In addition to signaling via $Ca^{2+}$, CD38 signaling occurs via cross-talk with antigen-receptor complexes on T- and B-cells or other types of receptor complexes, e.g., MHC molecules, involving CD38 in several cellular responses, but also in switching and secretion of IgG1.

CD38 is a type II transmembrane glycoprotein expressed on hemopoietic cells such as medullary thymocytes, activated T- and B-cells, resting NK cells and monocytes, lymph node germinal center lymphoblasts, plasma B cells, intrafollicular cells and dendritic cells. A portion of normal bone marrow cells, particular precursor cells as well as unbilical cord cells are CD38-positive. In addition to lymphoid precursor cells, CD38 is expressed on erythrocytes and on platelets, and expression is also found in some solid tissues such as gut, brain, prostate, bone, and pancreas. Mature resting T- and B-cells express limited to no surface CD38.

CD38 is also expressed in a variety of malignant hematological diseases, including multiple myeloma, leukemias and lymphomas, such as B-cell chronic lymphocytic leukemia, T- and B-cell acute lymphocytic leukemia, Waldenstrom macroglobulinemia, primary systemic amyloidosis, mantle-cell lymphoma, pro-lymphocytic/myelocytic leukemia, acute myeloid leukemia, chronic myeloid leukemia, follicular lymphoma, Burkitt's lymphoma, large granular lymphocytic (LGL) leukemia, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression may be involved, include, e.g., broncho-epithelial carcinomas of the lung, breast cancer (evolving from malignant proliferation of epithelial lining in ducts and lobules of the breast), pancreatic tumors evolving from the β-cells (insulinomas), tumors evolving from epithelium in the gut (e.g., adenocarcinoma and squamous cell carcinoma), carcinoma in the prostate gland, and seminomas in testis and ovarian cancers. In the central nervous system, neuroblastomas express CD38.

B-cell malignancies may arise in all lymphoid tissues where B-cells are normally being produced. Most patients with B-cell malignancies are initially diagnosed with disease involving bone marrow or lymph nodes. In the case of bone marrow involvement, the transformed B cells frequently circulate through the blood and become widely disseminated throughout peripheral lymphoid tissues. However, B-cell malignancies may also arise in some nonlymphoid tissues such as the thyroid, gastrointestinal tract, salivary glands and conjunctiva.

Well known B-cell malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related Non-Hodgkin's Lymphoma (NHL). B-cell malignancies comprise more than 85% of diagnosed lymphomas.

NHL is a broad classification of lymphomas originating from the lymphatic system when lymphocytes (B-cells or T-cells) become malignant and proliferate uncontrollably to form a tumor mass. In total, NHL encompasses around 30 different subtypes of lymphoma with a range of phenotypes and prognoses. It is projected that the incidence of NHL will reach over 140,000 in the major market countries by 2019.

Diffuse Large B-cell Lymphoma (DLBCL) is an aggressive most common subtype of NHL, accounting for 30-40% of lymphoid malignancy, and encompasses a biologically and clinically diverse set of diseases. Gene expression profiling studies suggest that DLBCL can be separated into two groups on the basis of gene expression profiles; these groups are known as germinal center B-cell like (GCB) and activated B-cell-like (ABC) lymphomas.

The standard of care for treatment of DLBCL is commonly called CHOP, a combination of cyclophosphamide, hydroxydaunorubicin (doxorubicin), vincristine and prednisone, or R-CHOP, a combination of anti-CD20 antibody rituximab and CHOP. In addition, following remission, hematopoietic stem cell transplantation may be considered.

Despite the current treatment options, the survival rates within high risk groups of aggressive NHL can be as low as 30% over 5 years. Therefore, there is a need for effective treatments and combination treatments for NHL and B-cell malignancies.

SUMMARY OF THE INVENTION

One embodiment of the invention is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces killing of CD38-expressing cells in vitro by antibody-dependent cell-mediated cytotoxicity (ADCC), antibody-dependent cellular phagocytosis (ADCP), complement dependent cytotoxicity (CDC), apoptosis, or modulation of CD38 enzymatic activity.

alone or in combination of CHOP or R-CHOP. Resected DLBCL tumors were implanted in SCID/Beige mice. Treatments were initiated when the tumors reached approximately 125-250 mm$^3$. Daratumumab was administered at 20 mg/kg once a week for three weeks. CHOP and R-CHOP were administered once on day 0 except prednisone was administered on days 0-4 using the following regimens: CHOP: (cyclophosphoamide (CTX): 30 mg/kg i.v.; doxorubicin: 2.5 mg/kg i.v; vincristine: 0.4 mg/kg i.v); prednisone: 0.15 mg/kg p.o; R-CHOP: rituximab 20 mg/kg i.p. DAY 0. Tumor volume was measured every three days. The Y-axis represents tumor volume±SEM.

Figure 1A:
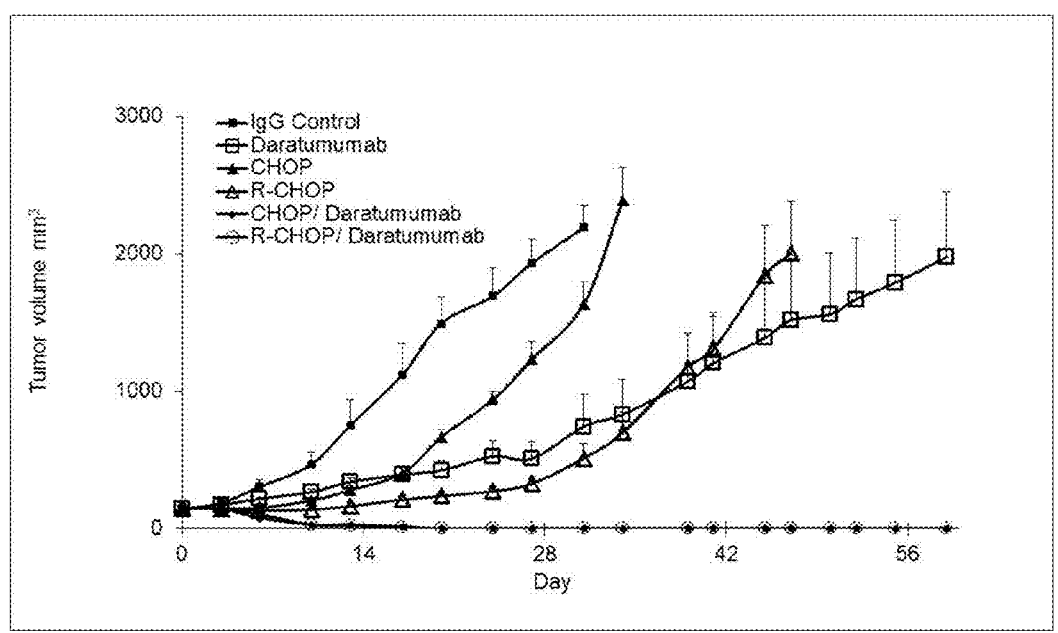
FIG. 1A shows efficacy of daratumumab in a patient-derived model of diffuse large B-cell lymphoma (DLBCL)
Figure 1B:
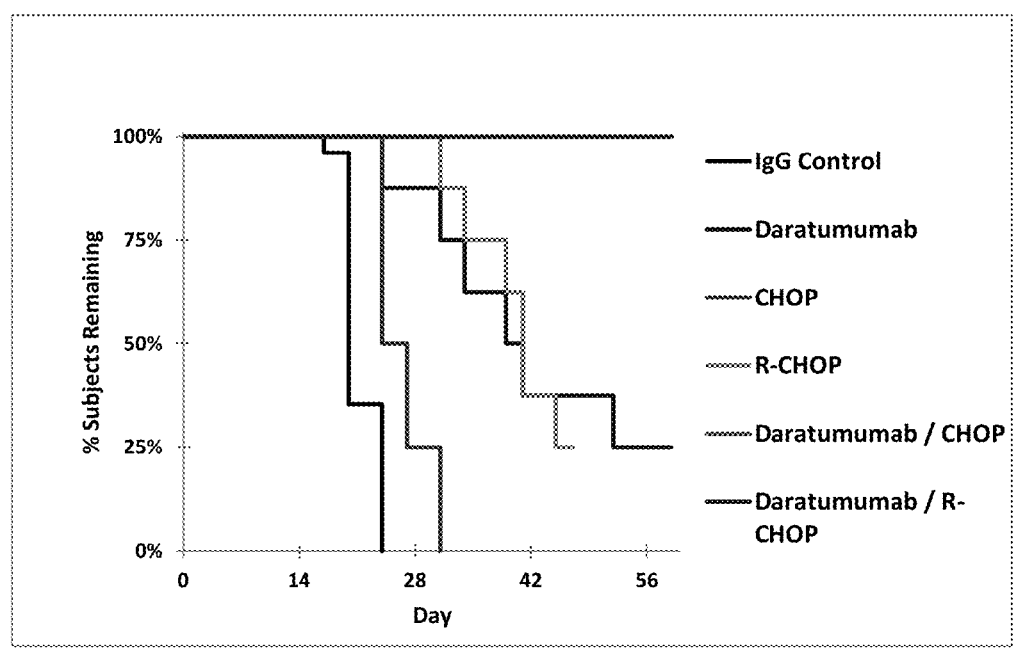

FIG. 1B shows the median survival time plotted against days after tumor inoculation of the study of FIG. 1A.

Figure 2:
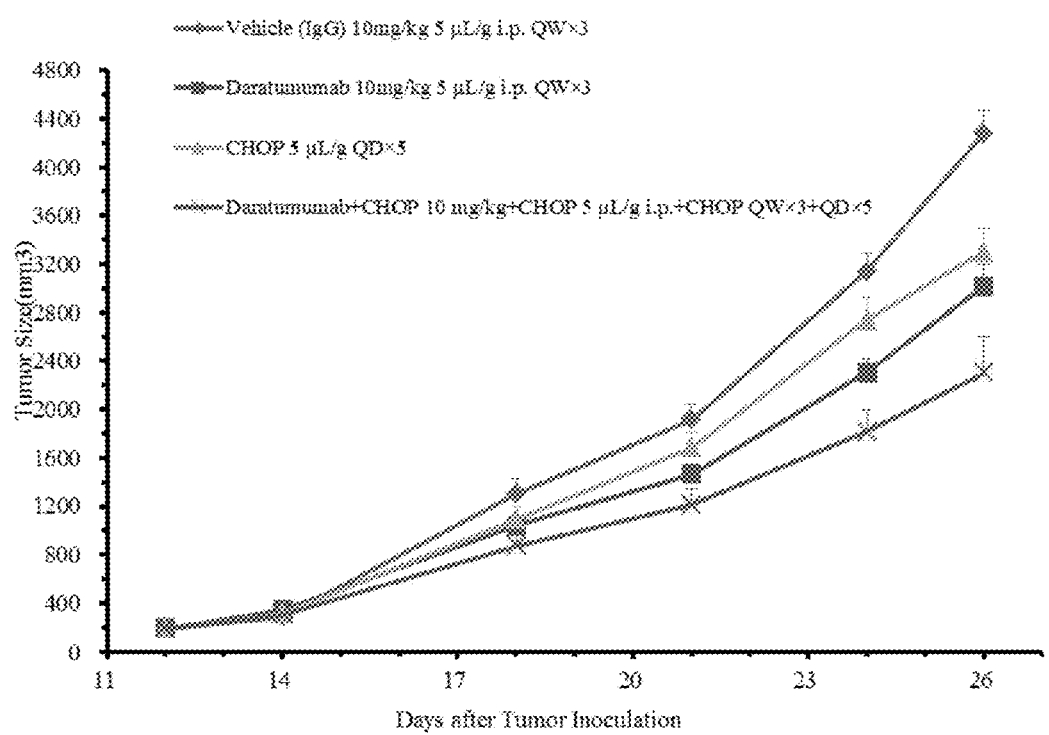
Figure 3:
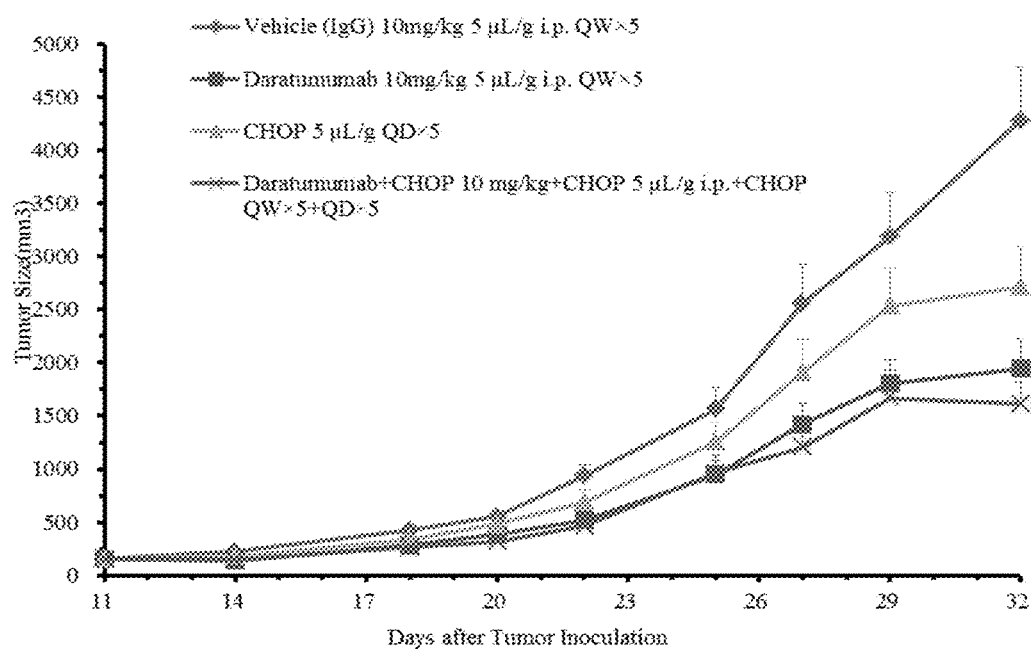

FIG. 2 shows efficacy of daratumumab in a preclinical model of non-Hodgkin's lymphoma alone or in combination with CHOP. 2×10$^5$ NAMALWA cells in matrigel were implanted into NOD SCID mice and treatment initiated when the main tumor size reached approximately 189 mm$^3$. Daratumumab was administered at 10 mg/kg once a week for three weeks. CHOP was administered daily on days 0-5 using following doses: cyclophosphoamide (CTX): 5 mg/kg i.v.; doxorubicin: 0.5 mg/kg i.v; vincristine: 0.08 mg/kg i.v., prednisone: 0.03 mg/kg p.o. Tumor volume was measured every three days. The Y-axis represents tumor volume±SEM FIG. 3 shows efficacy of daratumumab in a preclinical model of DLBCL alone or in combination with CHOP. 5×10$^6$ SU-DHL-6 cells were implanted into NOD SCID mice and treatment initiated when the main tumor size reached approximately 154 mm$^3$. Daratumumab was administered at 10 mg/kg once a week for four weeks. CHOP was administered daily on days 0-5 using following doses: cyclophosphoamide (CTX): 5 mg/kg i.v.; doxorubicin: 0.5 mg/kg i.v; vincristine: 0.08 mg/kg i.v., prednisone: 0.03 mg/kg p.o. Tumor size was plotted as Mean±SEM.

Figure 4:
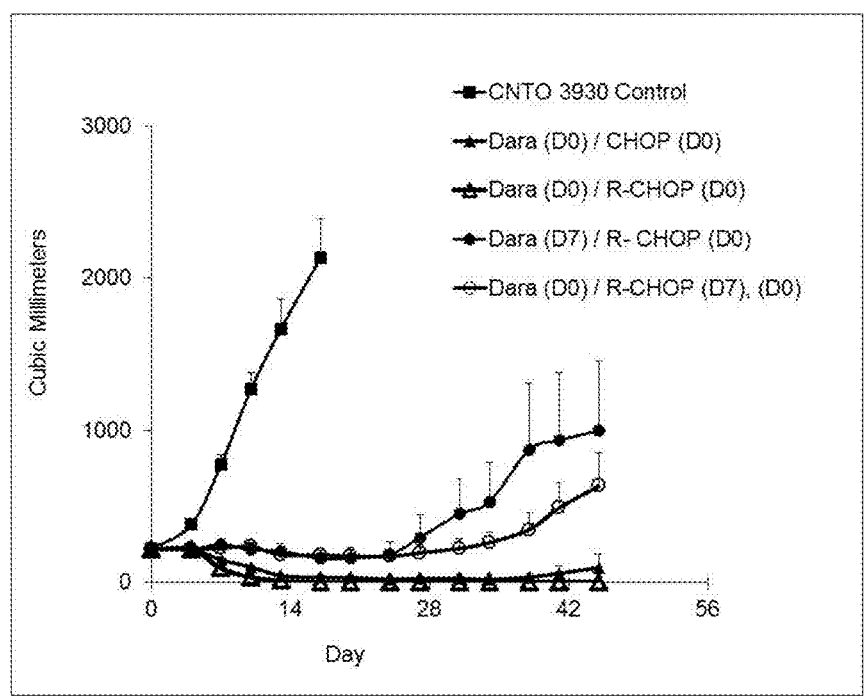

FIG. 4 shows efficacy of daratumumab in a patient-derived model of diffuse large B-cell lymphoma (DLBCL) in combination with CHOP or R-CHOP administered simultaneously or sequentially up to day 45 of the study. Daratumumab was administered at 20 mg/kg once a week for three weeks at day 0 or at day 7. CHOP was administered once on day 0 except prednisone was administered on days 0-4 using following regimens: CHOP: (cyclophosphoamide (CTX): 30 mg/kg i.v.; doxorubicin: 2.5 mg/kg i.v; vincristine: 0.4 mg/kg i.v); prednisone: 0.15 mg/kg p.o. Rituximab was administered at 20 mg/kg i.p. at either day 0 or day 7. Tumor size was plotted as Mean±SEM. CNTO3930: isotype control. Values in parenthesis indicate the day of dosing. The data represents results from an ongoing study at day 44.

Figure 5:
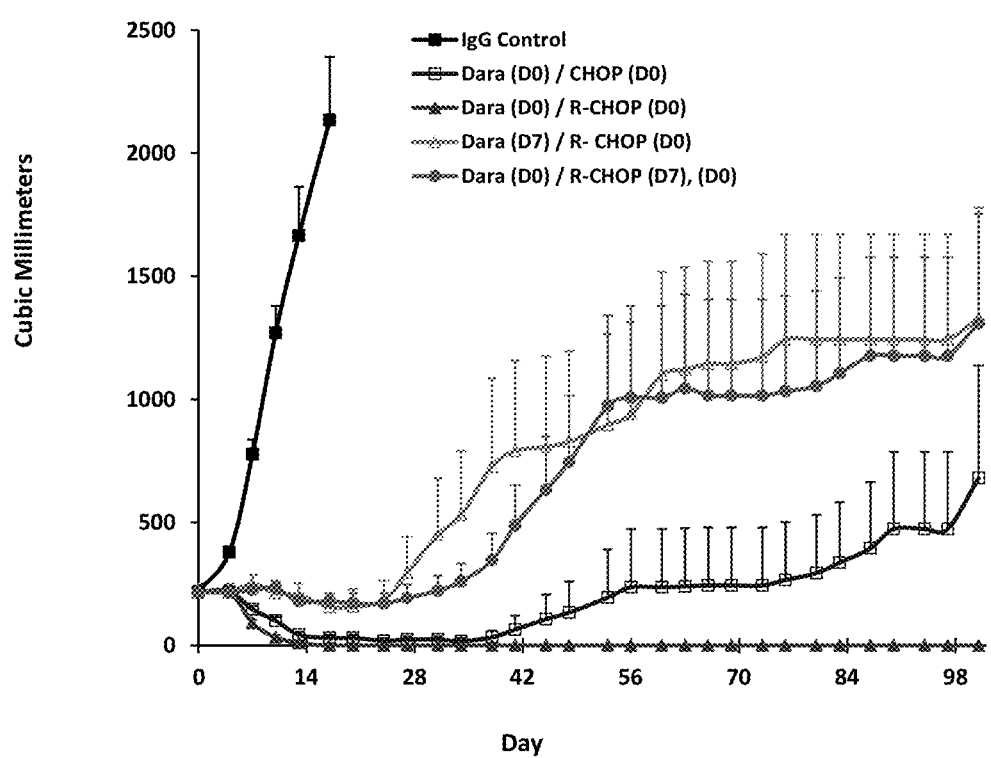

FIG. 5 shows efficacy of daratumumab in a patient-derived model of DLBCL in combination with CHOP or R-CHOP administered simultaneously or sequentially up to day 101 of the study. Dosing was as in FIG. 4. Tumor size was plotted as Mean±SEM. CNTO3930: isotype control. Values in parenthesis indicate the day of dosing. Statistical differences in tumor volume were determined using a two-tailed, one-way ANOVA followed by Dunnett's multiple comparisons test comparing treated single-agent groups with control and combinations with standard agent. *$P<0.05$ versus control, †$P<0.05$ versus CHOP, cyclophosphamide, doxorubicin, vincristine, and prednisone; DLBCL, diffuse large B-cell lymphoma, IHC, immunohistochemistry; i.v., intravenous; i.p., intraperitoneal.

DETAILED DESCRIPTION OF THE INVENTION

"CD38" refers to the human CD38 protein (synonyms: ADP-ribosyl cyclase 1, cADPr hydrolase 1, Cyclic ADP-ribose hydrolase 1). Human CD38 has an amino acid sequence shown in SEQ ID NO: 1

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes IgA$_1$, IgA$_2$, IgG$_1$, IgG$_2$, IgG$_3$ and IgG$_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains; a F(ab)$_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a domain antibody (dAb) fragment (Ward et al., Nature 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

The phrase "isolated antibody" refers to an antibody or antibody fragment that is substantially free of other antibodies having different antigenic specificities (e.g., an antibody that specifically binds CD38. An isolated antibody that specifically binds CD38, however, can have cross-reactivity to other antigens, such as orthologs of human CD38 such as *Macaca fascicularis* (cynomolgus) CD38. Moreover, an isolated antibody may be substantially free of other cellular material and/or chemicals.

An antibody variable region consists of a "framework" region interrupted by three "antigen binding sites". The antigen binding sites are defined using various terms such as Complementarity Determining Regions (CDRs), three in the VH (HCDR1, HCDR2, HCDR3), and three in the VL (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991) or "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin where the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A human antibody may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

The term "monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitutions, insertions or deletions.

"Synergy", "synergism" or "synergistic" mean more than the expected additive effect of a combination.

The term "in combination with" as used herein means that two or more therapeutics can be administered to a subject together in a mixture, concurrently as single agents or sequentially as single agents in any order.

The terms "treat" or "treatment" refers to both therapeutic treatment and prophylactic or preventative measures, wherein the object is to prevent or slow down (lessen) an undesired physiological change or disorder, such as the development or spread of tumor or tumor cells. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Inhibits growth" (e.g., referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth can occur by a variety of mechanisms, for example by antibody-dependent cell-mediated toxicity (ADCC), antibody dependent cellular phagocytosis (ADCP), complement dependent cytotoxicity (CDC), apoptosis, necrosis, or inhibition of cell proliferation.

A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient, reduction of a tumor burden, arrested or slowed growth of a tumor, and/or absence of metastasis of cancer cells to other locations in the body.

The invention provides methods for treating patients having CD38-positive hematological malignancy. The invention is based on the discovery that an anti-CD38 antibody administered in combination with CHOP or R-CHOP provides a synergistically potent therapeutic efficacy in vivo in relevant tumor models of hematological malignancy.

One embodiment of the invention disclosed herein, including in the numbered embodiments listed below, is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces killing of CD38-expressing cells in vitro by antibody-dependent cell-mediated cytotoxicity (ADCC), antibody dependent cellular phagocytosis (ADCP), complement dependent cytotoxicity (CDC), apoptosis, or modulation of CD38 enzymatic activity.

In some embodiments of the invention disclosed herein, including in the numbered embodiments listed below, the anti-CD38 antibody induces in vitro killing of the CD38-expressing cells by ADCC or CDC.

"CD38-positive hematological malignancy" refers to a hematological malignancy characterized by the presence of tumor cells expressing CD38 including leukemias, lymphomas and myeloma. Examples of such CD38-positive hematological malignancies include precursor B-cell lymphoblastic leukemia/lymphoma and B-cell non-Hodgkin's lymphoma; acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma, plasma cell leukemia, post-transplant lymphoproliferative disorder, Waldenstrom's macroglobulinemia, plasma cell leukemias and anaplastic large-cell lymphoma (ALCL).

In one embodiment of the invention disclosed herein, including in the numbered embodiments listed below, the CD-38 positive hematological malignancy is multiple myeloma.

In one embodiment of the invention disclosed herein, including in the numbered embodiments listed below, the CD-38 positive hematological malignancy is diffuse large B-cell lymphoma (DLBCL).

In one embodiment of the invention disclosed herein, including in the numbered embodiments listed below, the CD-38 positive hematological malignancy is non-Hodgkin's lymphoma.

In one embodiment of the invention disclosed herein, including in the numbered embodiments listed below, the CD-38 positive hematological malignancy is acute lymphoblastic leukemia (ALL).

In one embodiment of the invention disclosed herein, including in the numbered embodiments listed below, the CD-38 positive hematological malignancy is follicular lymphoma (FL).

In one embodiment of the invention disclosed herein, including in the numbered embodiments listed below, the CD-38 positive hematological malignancy is Burkitt's lymphoma (BL).

In one embodiment of the invention disclosed herein, including in the numbered embodiments listed below, the CD-38 positive hematological malignancy is mantle cell lymphoma (MCL).

In one embodiment of the invention disclosed herein, including in the numbered embodiments listed below, the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In one embodiment of the present invention, including in the numbered embodiments listed below the disorder involving cells expressing CD38 is Hodgkin's lymphoma.

Other examples of disorders involving cells expressing CD38 include malignancies derived from T and NK cells including: mature T cell and NK cell neoplasms including T-cell prolymphocytic leukemia, T-cell large granular lymphocytic leukemia, aggressive NK cell leukemia, adult T-cell leukemia/lymphoma, extranodal NK/T cell lymphoma, nasal type, 78 enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

Any anti-CD38 antibody may be used in the methods of the invention as disclosed herein, including in the numbered embodiments listed below, provided that the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or modulation of CD38 enzymatic activity. The variable regions of the anti-CD38 antibodies may be obtained from existing anti-CD38 antibodies, and cloned as full length antibodies using standard methods. Exemplary variable regions binding CD38 that may be used are described, e.g., in Intl. Pat. Publ. Nos. WO05/103083, WO06/125640, WO07/042309, WO08/047242, WO12/092612, WO06/099875 and WO11/154453A1.

An exemplary anti-CD38 antibody that may be used is daratumumab. Daratumumab comprises heavy chain variable region (VH) and a light chain variable region (VL) amino acid sequences shown in SEQ ID NO: 4 and 5, respectively, heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, and is of IgG1/κ subtype. Daratumumab heavy chain amino acid sequence is shown in SEQ ID NO: 12 and light chain amino acid sequence shown in SEQ ID NO: 13.

SEQ ID NO: 1
MANCEFSPVSGDKPCCRLSRRAQLCLGVSILVLILVVVLAVVVPRWRQQW SGPGTTKRFPETVLARCVKYTEIHPEMRHVDCQSVWDAFKGAFISKHPCN ITEEDYQPLMKLGTQTVPCNKILLWSRIKDLAHQFTQVQRDMFTLEDTLL GYLADDLTWCGEFNTSKINYQSCPDWRKDCSNNPVSVFWKTVSRRFAEAA CDVVHVMLNGSRSKIFDKNSTFGSVEVHNLQPEKVQTLEAWVIHGGREDS RDLCQDPTIKELESIISKRNIQFSCKNIYRPDKFLQCVKNPEDSSCTSEI

SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVSA ISGSGGGTYYADSVKGRFTISRDNSKNTLYLQMNSLRAEDTAVYFCAKDK ILWFGEPVFDYWGQGTLVTVSS

SEQ ID NO: 5
EIVLTQSPATLSLSPGERATLSCRASQSVSSYLAWYQQKPGQAPRLLIYD ASNRATGIPARFSGSGSGTDFTLTISSLEPEDFAVYYCQQRSNWPPTFGQ GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVSA ISGSGGGTYYADSVKGRFTISRDNSKNTLYLQMNSLRAEDTAVYFCAKDK ILWFGEPVFDYWGQGTLVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPP KPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GK

SEQ ID NO: 13
EIVLTQSPATLSLSPGERATLSCRASQSVSSYLAWYQQKPGQAPRLLIYD ASNRATGIPARFSGSGSGTDFTLTISSLEPEDFAVYYCQQRSNWPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC

Another exemplary anti-CD38 antibody that may be used is mAb003 comprising the VH and VL sequences of SEQ ID NOs: 14 and 15, respectively and described in U.S. Pat. No. 7,829,693.

SEQ ID NO: 14
QVQLVQSGAEVKKPGSSVKVSCKASGGTFSSYAFSWVRQAPGQGLEWMGR VIPFLGIANSAQKFQGRVTITADKSTSTAYMDLSSLRSEDTAVYYCARDD IAALGPFDYWGQGTLVTVSSAS

SEQ ID NO: 15
DIQMTQSPSSLSASVGDRVTITCRASQGISSWLAWYQQKPEKAPKSLIYA ASSLQSGVPSRFSGSGSGTDFTLTISSLQPEDFATYYCQQYNSYPRTFGQ GTKVEIK

Another exemplary anti-CD38 antibody that may be used is mAb024 comprising the VH and VL sequences of SEQ ID NOs: 16 and 17, respectively, described in U.S. Pat. No. 7,829,693.

SEQ ID NO: 16
EVQLVQSGAEVKKPGESLKISCKGSGYSFSNYWIGWVRQMPGKGLEWMGI IYPHDSDARYSPSFQGQVTFSADKSISTAYLQWSSLKASDTAMYYCARHV GWGSRYWYFDLWGRGTLVTVSS

SEQ ID NO: 17
EIVLTQSPATLSLSPGERATLSCRASQSVSSYLAWYQQKPGQAPRLLIYD ASNRATGIPARFSGSGSGTDFTLTISSLEPEDFAVYYCQQRSNWPPTFGQ GTKVEIK

Another exemplary anti-CD38 antibody that may be used is MOR-202 (MOR-03087) comprising the VH and VL sequences of SEQ ID NOs: 18 and 19, respectively, described in U.S. Pat. No. 8,088,896.

SEQ ID NO: 18
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS

SEQ ID NO: 19
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ

Anti-CD38 antibodies used in the methods of the invention disclosed herein, including in the numbered embodiments listed below, may also be selected de novo from, e.g., a phage display library, where the phage is engineered to express human immunoglobulins or portions thereof such as Fabs, single chain antibodies (scFv), or unpaired or paired antibody variable regions (Knappik et al., J Mol Biol 296: 57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from e.g., phage display libraries expressing antibody heavy and light chain variable regions as fusion proteins with bacteriophage pIX coat protein as described in Shi et al., J. Mol. Biol. 397:385-96, 2010 and PCT Intl. Publ. No. WO09/085462). The antibody libraries can be screened for binding to human CD38 extracellular domain, obtained positive clones further characterized, Fabs isolated from the clone lysates, and subsequently cloned as full length antibodies. Such phage display methods for isolating human antibodies are established in the art. See for example: U.S. Pat. No. 5,223,409; U.S. Pat. No. 5,403,484; and U.S. Pat. No. 5,571,698, U.S. Pat. No. 5,427,908, U.S. Pat. No. 5,580,717, U.S. Pat. No. 5,969,108, U.S. Pat. No. 6,172,197, U.S. Pat. No. 5,885,793; U.S. Pat. No. 6,521,404; U.S. Pat. No. 6,544,731; U.S. Pat. No. 6,555,313; U.S. Pat. No. 6,582,915; and U.S. Pat. No. 6,593,081.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such functions may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, e.g., CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In the methods described herein, and in some embodiments of each and every one of the numbered embodiments listed below, the anti-CD38 antibody is of IgG1, IgG2, IgG3 or IgG4 isotype.

In the methods described herein, and in some embodiments of each and every one of the numbered embodiments listed below, the anti-CD38 antibody induces in vitro killing of CD38-expressing cells by ADCC.

In the methods described herein, and in some embodiments of each and every one of the numbered embodiments listed below, the anti-CD38 antibody induces in vitro killing of CD38-expressing cells by CDC.

In the methods described herein, and in some embodiments of each and every one of the numbered embodiments listed below, the anti-CD38 antibody induces killing of CD38-expressing cells by ADCP in vitro.

In the methods described herein, and in some embodiments of each and every one of the numbered embodiments listed below, the anti-CD38 antibody induces killing of CD38-expressing cells by apoptosis in vitro.

In the methods described herein, and in some embodiments of each and every one of the numbered embodiments listed below, the anti-CD38 antibody induces killing of CD38-expressing cells by ADCC and CDC in vitro.

While not wishing to be bound to any particular theory on mechanism of action, it is expected that the anti-CD38 antibody of the invention will induce in vivo killing of CD38-expressing cells by ADCC, CDC, ADCP, apoptosis or in vivo modulation of CD38 enzymatic activity.

"Antibody-dependent cellular cytotoxicity," or "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD38-expressing cells, occurs as a result of effector cell activity through the secretion of membrane pore-forming proteins and proteases. To assess ADCC activity of an anti-CD38 antibody in vitro, the antibody may be added to CD38-expressing cells in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Exemplary effector cells for such assays include peripheral blood mononuclear cells (PBMC) and NK cells. Exemplary target cells include Daudi cells (ATCC® CCL-213™) or B cell leukemia or lymphoma tumor cells expressing CD38. In an exemplary assay, target cells are labeled with 20 μCi of $^{51}$Cr for 2 hours and washed extensively. Cell concentration of the target cells can be adjusted to $1 \times 10^6$ cells/ml, and anti-CD38 antibodies at various concentrations are added. Assays are started by adding Daudi cells at an effector:target cell ratio of 40:1. After incubation for 3 hr at 37° C. assays are stopped by centrifugation, and $^{51}$Cr release from lysed cells are measured in a scintillation counter. Percentage of cellular cytotoxicity may be calculated as % maximal lysis which may be induced by adding 3% perchloric acid to target cells. Anti-CD38 antibodies used in the methods of the invention may induce ADCC by about 20%, 25%, 30%, 35%, 40%, 45%, 50%, 55%, 60%, 65%, 70%, 75%, 80%, 85%, 90%, 95% or 100% of control (cell lysis induced by 3% perchloric acid).

"Antibody-dependent cellular phagocytosis" ("ADCP") refers to a mechanism of elimination of antibody-coated target cells by internalization by phagocytic cells, such as macrophages or dentricit cells. In vitro ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecule. Effctor:target cell ratio may be for example 4:1.

Effector cells may be incubated with target cells for 4 hours with or without anti-CD38 antibody. After incubation, cells may be detached using accutase. Macrophages can be identified with anti-CD11b and anti-CD14 antibodies coupled to a fluorescent label, and percent phagocytosis can be determined based on % GFP fluorescent in the CD11$^+$CD14$^+$ macrophages using standard methods. Anti-CD38 antibodies used in the methods of the invention may induce ADCP by about 20%, 25%, 30%, 35%, 40%, 45%, 50%, 55%, 60%, 65%, 70%, 75%, 80%, 85%, 90%, 95% or 100%.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD38-expressing cells can be measured in vitro for example by plating Daudi cells at 1×10$^5$ cells/well (50 μl/well) in RPMI-B (RPMI supplemented with 1% BSA), adding 50 μl anti-CD38 antibodies to the wells at final concentration between 0-100 incubating the reaction for 15 min at room temperature, adding 11 μl of pooled human serum to the wells, and incubation the reaction for 45 min at 37° C. Percentage (%) lysed cells may be detected as % propidium iodide stained cells in FACS assay using standard methods. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%

The ability of monoclonal antibodies to induce ADCC can be enhanced by engineering their oligosaccharide component. Human IgG1 or IgG3 are N-glycosylated at Asn297 with the majority of the glycans in the well known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such antibodies can be achieved using different methods reported to lead to the expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-40, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng 88:901-908, 2004), or co-expression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are, for example, substitutions at amino acid positions 256, 290, 298, 312, 356, 330, 333, 334, 360, 378 or 430 (residue numbering according to the EU index) as described in U.S. Pat. No. 6,737,056.

In some methods described herein, and in some embodiments of each and every one of the numbered embodiments listed below, the anti-CD38 antibodies comprise a substitution in the antibody Fc.

In some methods described herein, and in some embodiments of each and every one of the numbered embodiments listed below, the anti-CD38 antibodies comprise a substitution in the antibody Fc at amino acid positions 256, 290, 298, 312, 356, 330, 333, 334, 360, 378 or 430 (residue numbering according to the EU index).

Another embodiment of the invention, including in the numbered embodiments listed below, is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the anti-CD38 antibody competes for binding to CD38 with an antibody comprising a heavy chain variable region (VH) of SEQ ID NO: 4 and a light chain variable region (VL) of SEQ ID NO: 5 (daratumumab).

Antibodies can be evaluated for their competition with daratumumab having VH of SEQ ID NO: 4 and VL of SEQ ID NO: 5 for binding to CD38 using well known in vitro methods. In an exemplary method, CHO cells recombinantly expressing CD38 may be incubated with unlabeled daratumumab for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of unlabelled daratumumab may be added for about 15 minutes and subsequently biotinylated test antibodies may be added. After washes in PBS/Tween, binding of the test biotinylated antibodies may be detected using horseradish peroxidase (HRP)-conjugated streptavidine and the signal detected using standard methods. It is readily apparent that in the competition assays, daratumumab may be labelled and the test antibody unlabeled. The test antibody competes with daratumumab when daratumumab inhibits binding of the test antibody, or the test antibody inhibits binding of daratumumab by 20%, 30%, 40%, 50%, 60%, 70%, 80%, 85%, 90%, 95% or 100%. The epitope of the test antibody can further be defined, for example, by peptide mapping or hydrogen/deuterium protection assays using known methods.

Another embodiment of the invention disclosed herein, including in the numbered embodiments listed below, is a method of treating a subject having a CD38-positive hematological malignancy, comprising administering to a patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity. The epitope of the antibody includes some or all of the residues in these regions having the sequences shown in SEQ ID NO: 2 or SEQ ID NO: 3. In some embodiments disclosed herein, including in the numbered embodiments listed below, the antibody epitope comprises at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments disclosed herein, including in the numbered embodiments listed below, the antibody epitope comprises at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments disclosed herein, including in the numbered embodiments listed below, the antibody epitope comprises at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1). In some embodiments disclosed herein, including in the numbered embodiments listed below, the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

In some embodiments of the invention described herein, and in some embodiments of each and every one of the numbered embodiments listed below, the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) or minimally to residues KRN and VQLT (SEQ ID NO: 20) as shown above is daratumumab having certain VH, VL and CDR sequences as described above. Antibodies that bind to the region SKRNIQFSCKNIYR (SEQ ID NO: 2) and the region EKVQTLEAWVIHGG (SEQ ID NO: 3) of human CD38 (SEQ ID NO: 1) can be generated, for example, by immunizing mice with peptides having the amino acid sequences shown in SEQ ID NOs: 2 and 3 using standard methods and as described herein. Antibodies can be further evaluated, for example, by assaying competition between daratumumab and a test antibody for binding to CD38 as described above.

In the methods described herein, and in some embodiments of each and every one of the numbered embodiments listed below, the anti-CD38 antibody can bind human CD38 with a range of affinities ($K_D$). In one embodiment according to the invention, and in some embodiments of each and every one of the numbered embodiments listed below, the anti-CD38 antibody binds to CD38 with high affinity, for example, with a $K_D$ equal to or less than about $10^{-7}$M, such as but not limited to, 1-9.9 (or any range or value therein, such as 1, 2, 3, 4, 5, 6, 7, 8, or 9)$\times 10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art. One exemplary affinity is equal to or less than $1 \times 10^{-8}$ M. Another exemplary affinity is equal to or less than $1 \times 10^{-9}$ M.

In some methods described herein, and in some embodiments of each and every one of the numbered embodiments listed below, the anti-CD38 antibody has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some methods described herein, and in some embodiments of each and every one of the numbered embodiments listed below, the anti-CD38 antibody has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or 'normal fucose content" as used herein refers to antibodies with fucose content of about over 50%, typically about over 60%, 70%, 80% or over 85%.

The anti-CD38 antibodies used in the methods, and in some embodiments of each and every one of the numbered embodiments listed below, may induce CD38-positive cell killing in vitro by apoptosis. Methods for evaluating apoptosis are well known, and include for example annexin IV staining using standard methods. The anti-CD38 antibodies used in the methods of the invention may induce apoptosis in about 20%, 25%, 30%, 35%, 40%, 45%, 50%, 55%, 60%, 65%, 70%, 75%, 80%, 85%, 90%, 95% or 100% of cells.

The anti-CD38 antibodies used in the methods, and in some embodiments of each and every one of the numbered embodiments listed below, may induce CD38-positive cell killing by modulation of CD38 enzymatic activity. CD38 is a multifunctional ectoenzme with ADP-ribosyl cyclase 1 activity catalyzing the formation of cyclic ADP-ribose (cADPR) and ADPR from NAD and also functions to hydrolyze $NAD^+$ and cADPR to ADPR. CD38 also catalyzes the exchange of the nicotinamide group of $NADP^+$ with nicotinic acid under acidic conditions, to yield $NAADP^+$ (nicotinic acid-adenine dinucleotide phosphate). Modulation of the enzymatic activity of human CD38 with anti-CD38 antibodies used in the methods of the invention may be measured in an assay described in Graeff et al., J. Biol. Chem. 269, 30260-30267 (1994). For example, substrate $NGD^+$ may be incubated with CD38, and the modulation of the production of cyclic GDP-ribose (cGDPR) may be monitored spectrophotometrically at excitation at 340 nM and emission at 410 nM at different time points after addition of the antibody at various concentrations. Inhibition of the synthesis of cADPR may be determined according to the HPLC method described in Munshi et al., J. Biol. Chem. 275, 21566-21571 (2000). The anti-CD38 antibodies used in the methods of the invention may inhibit CD38 enzymatic activity by at least about 20%, 25%, 30%, 35%, 40%, 45%, 50%, 55%, 60%, 65%, 70%, 75%, 80%, 85%, 90%, 95% or 100%.

In some methods of the invention described herein, and in some embodiments of each and every one of the numbered embodiments listed below, the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively.

In some methods of the invention described herein, and in some embodiments of each and every one of the numbered embodiments listed below, the anti-CD38 antibody comprises the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain variable region (VH) of SEQ ID NO: 4 and the light chain variable region (VL) of SEQ ID NO: 5.

In some methods of the invention described herein, and in some embodiments of each and every one of the numbered embodiments listed below, the anti-CD38 antibody comprises a heavy chain of SEQ ID NO: 12 and a light chain of SEQ ID NO: 13.

In some methods of the invention described herein, and in some embodiments of each and every one of the numbered embodiments listed below, the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

Antibodies that are substantially identical to the antibody comprising the heavy chain of SEQ ID NO: 12 and the light chain of SEQ ID NO: 13 may be used in the methods of the invention, and in some embodiments of each and every one of the numbered embodiments listed below. The term "substantially identical" as used herein means that the two antibody heavy chain or light chain amino acid sequences being compared are identical or have "insubstantial differences." Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings. Exemplary substitutions that can be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis in vitro using methods described herein.

In some embodiments, and in some embodiments of each and every one of the numbered embodiments listed below, the anti-CD38 antibody is a bispecific antibody. The VL and/or the VH regions of the existing anti-CD38 antibodies or the VL and VH regions identified de novo as described above may be engineered into bispecific full length antibodies. Such bispecific antibodies may be made by modulating the CH3 interactions between the two monospecific antibody heavy chains to form bispecific antibodies using technologies such as those described in U.S. Pat. No. 7,695,936; Int. Pat. Publ. No. WO04/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. No. 5,932,448; U.S. Pat. No. 6,833,441).

Another embodiment of the invention is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the CD38- positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

A therapeutic regimen of the anti-CD38 antibody in combination with cyclophosphamide, doxorubicin, vincristine and prednisone (CHOP) can provide a synergistic efficacy in in vivo tumor killing when compared to the standard of care CHOP or R-CHOP, and therefore can provide a benefit in a patient population when compared to CHOP or R-CHOP used alone.

The invention also provides for a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is resistant to or has acquired resistance to treatment with at least one chemotherapeutic agent or a combination of at least one chemotherapeutic agent and an anti-CD20 antibody.

The invention also provides for a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject has discontinued treatment with at least one chemotherapeutic agent or a combination of at least one chemotherapeutic agent and an anti-CD20 antibody due to side-effects.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is cyclophosphamide, doxorubicin, vincristine, prednisone, ifosfamide, carboplatin or etoposide.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is a combination of cyclophosphamide, doxorubicin, vincristine and prednisone (CHOP).

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is a combination of ifosfamide, carboplatin and etoposide (ICE).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the anti-CD 20 antibody is rituximab.

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of cyclophosphamide, doxorubicin, vincristine and prednisone (CHOP), and the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of ifosfamide, carboplatin and etoposide (ICE), and the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of cyclophosphamide, doxorubicin, vincristine and prednisone (CHOP) and the anti-CD20 antibody is rituximab.

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of ifosfamide, carboplatin and etoposide (ICE), and the anti-CD20 antibody is rituximab.

Various qualitative and/or quantitative methods may be used to determine if a subject is resistant, has developed or is susceptible to developing a resistance to treatment with at least one chemotherapeutic agent or a combination of at least one chemotherapeutic agent and an anti-CD20 antibody. Symptoms that may be associated with resistance include, for example, a decline or plateau of the well-being of the patient, an increase in the size of a tumor, increase in the number of cancer cells, arrested or slowed decline in growth of a tumor or tumor cells, and/or the spread of cancerous cells in the body from one location to other organs, tissues or cells. Re-establishment or worsening of various symptoms associated with tumor may also be an indication that a subject has developed or is susceptible to developing resistance to at least one chemotherapeutic agent and an anti-CD20 antibody. The symptoms associated with cancer may vary according to the type of cancer. For example, symptoms associated with B-cell malignanices may include swollen lymp nodes in neck, groin or armpits, fever, night sweats, coughing, chest pain, unexplained weight loss, abdominal swelling or pain, or a feeling of fullness. Remission in malignant lymphomas is standardized using the Cheson criteria (Cheson et al., J Clin Oncology 25:579-586, 2007), which guidelines can be used to determine if a subject has developed a resistance to at least one chemotherapeutic agent or a combination of at least one chemotherapeutic agent and an anti-CD20 antibody.

The heavy and light chain amino acid sequences of the antibodies identified by their United States Adopted Names (USAN) are typically available via the American Medical Association at http://_www_ama-assn_org or via the CAS registry, or at International Nonproprietary Names (INN) at http://_www_drugs_com/inn_html.

In some embodiments of the invention described herein, and in some embodiments of each and every one of the numbered embodiments listed below, the subject having a CD38-positive hematological malignancy is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277:26733-40, 2002). Patients can be analyzed for their FcγRIIIa polymorphism using routine methods.

The invention also provides for the method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is homozygous for phenylalanine at position 158 of CD16 or heterozygous for valine and pheynylalanine at position 158 of CD16.

Administration/Pharmaceutical Compositions

In the methods of the invention, and in some embodiments of each and every one of the numbered embodiments listed below, the anti-CD38 antibodies may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the anti-CD38 antibody in the methods of the invention may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention, and in some embodiments of each and every one of the numbered embodiments listed below, may be administered to a patient by any suitable route, for example parentally by intravenous (i.v.) infusion or bolus injection, intramuscularly or subcutaneously or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to a patient having a CD38-positive hematological malignancy is sufficient to alleviate or at least partially arrest the disease being treated ("therapeutically effective amount") and may be sometimes 0.005 mg/kg to about 100 mg/kg, e.g. about 0.05 mg/kg to about 30 mg/kg or about 5 mg to about 25 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat a CD38-positive B-cell malignancy, but 9, 10, 11, 12, 13, 14, 15, 16, 17, 18, 19, 20 or more doses may be given.

The administration of the anti-CD38 antibody in the methods of the invention and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-CD38 antibodies may be administered in the methods of the invention and in some embodiments of each and every one of the numbered embodiments listed below, by maintenance therapy, such as, e.g., once a week for a period of 6 months or more.

For example, anti-CD38 antibodies in the methods of the invention and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Anti-CD38 antibodies in the methods of the invention and in some embodiments of each and every one of the numbered embodiments listed below, may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody in the methods of the invention and in some embodiments of each and every one of the numbered embodiments listed below, may be lyophilized for storage and reconstituted in a suitable carrier prior to use. This technique has been shown to be effective with conventional protein preparations and well known lyophilization and reconstitution techniques can be employed.

The anti-CD38 antibody in the methods of the invention and in some embodiments of each and every one of the numbered embodiments listed below, may be administered in combination with cyclophosphamide, doxorubicin, vincristine and prednisone (CHOP).

For example, CHOP and the individual constituents thereof, can be administered as described, in Moharhmad et al., Gun. Cancer Res 25:4950, 2000; McKelvey et al., Cancer 1484-1493; 1976; Armitage et al., J. Clin. Oncol. 2:898-902, 1984; Skeet, R. T., Handbook of Cancer Gliemotherapy, 3rd Edition, Little, Brown & Co., 1991:343. Typical routes of administration are intraperitoneal (i.p.), intravenous (i.v.) or oral (p.o.). Regimens may be either daily, every other day or every fourth day. Typical doses of the CHOP components are as follows: cyclophosphamide, up to 30 mg/kg single dose i.v. or i.p., or 20 mg/kg daily for eight days i.v. or i.p.; doxorubicin, up to 6 mg/kg single does i.v. or i.p.; vincristine, 0.2 to 0.5 mg/kg single dose i.p. or i.v.; prednisone, up to 10 mg/kg/day as a single agent, p.o.

For example CHOP may be administered at doses: cyclophosphamide 30 mg/kg, doxorubicin 2.5 mg/kg, vincristine 0.4 mg/kg prednisone 0.15 mg/kg. CHOP may be given every 21 days for different number of cycles. Cyclopshophamide, doxorubicin and vincristine may be given as i.v. infusion. Prednisone may be given as a tablet, taken daily by mouth for five days at the beginning of each cycle.

In the methods of the invention and in some embodiments of each and every one of the numbered embodiments listed below, the combination of the anti-CD38 antibody and CHOP may be administered over any convenient timeframe. For example, the anti-CD38 antibody and CHOP may be administered to a patient on the same day, and even in the same intravenous infusion, except for prednisone. However, the anti-CD38 antibody and CHOP may also be administered on alternating days or alternating weeks or months, and so on. In some methods, the anti-CD38 antibody and CHOP may be administered with sufficient proximity in time that they are simultaneously present (e.g., in the serum) at detectable levels in the patient being treated. In some methods, an entire course of treatment with the anti-CD38 antibody consisting of a number of doses over a time period is followed or preceded by a course of treatment with CHOP, consisting of a number of doses. A recovery period of 1, 2 or several days or weeks may be used between administration of the anti-CD38 antibody and CHOP.

The anti-CD38 antibody in the methods of the invention and in some embodiments of each and every one of the numbered embodiments listed below, may be administered in combination with cyclophosphamide, doxorubicin, vincristine and prednisone (CHOP).

The anti-CD38 antibody in the methods of the invention and in some embodiments of each and every one of the numbered embodiments listed below, may be administered in combination with cyclophosphamide, doxorubicin, vincristine, prednisone and an anti-CD20 antibody rituximab (R-CHOP).

Rituximab may be given as an intravenous infusion at a dose of 375 mg/m$^2$ and may be administered once weekly for 4 or 8 doses.

The combination of anti-CD38 antibody and CHOP may be administered together with any form of radiotherapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon), and/or with surgery. Radiotherapy may be used in patients having bulky disease (tumor size over about 10 cm) or in a palliative setting for patients who are not candidates for chemotherapy.

While having described the invention in general terms, the embodiments of the invention will be further disclosed in the following examples that should not be construed as limiting the scope of the claims.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1. An anti-CD38 antibody for use in treating a subject having a CD38-positive hematological malignancy, in combination with cyclophosphamide, doxorubicin, vincristine and prednisone (CHOP).

2. Cyclophosphamide, doxorubicin, vincristine and prednisone (CHOP) for use in treating a subject having a CD38-positive hematological malignancy, in combination with an anti-CD38 antibody.

3. The combination of an anti-CD38 antibody, cyclophosphamide, doxorubicin, vincristine and prednisone (CHOP) for use in treating a subject having a CD38-positive hematological malignancy.

4. The anti-CD38 antibody for use according to embodiment 1, the CHOP for use according to embodiment 2, or the combination according to embodiment 3, wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, preferably wherein the anti-CD38 antibody induces killing of the CD38-expressing cells by ADCC or CDC in vitro.

5. The anti-CD38 antibody for use according to embodiment 1 or 4, the CHOP for use according to embodiment 2 or 4, or the combination for use according to embodiment 3 or 4, wherein the anti-CD38 antibody competes for binding to CD38 with an antibody comprising the heavy chain variable region (VH) of SEQ ID NO: 4 and the light chain variable region (VL) of SEQ ID NO: 5.

6. The anti-CD38 antibody for use according to embodiment 1, 4 or 5, the CHOP for use according to embodiment 2, 4 or 5, or the combination for use according to embodiment 3, 4 or 5, wherein the anti-CD38 antibody competes for binding to CD38 with an antibody comprising the heavy chain variable region (VH) of SEQ ID NO: 4 and the light chain variable region (VL) of SEQ ID NO: 5.

7. The anti-CD38 antibody for use according to any one of embodiments 1 or 4-6, the CHOP for use according to any one of embodiments 2 or 4-6, or the combination for use according to any one of embodiments 3-6, wherein the anti-CD38 antibody binds to an epitope comprising at least one amino acid in the region SKRNIQFSCKNIYR (SEQ ID NO: 2) and comprising at least one amino acid in the region EKVQTLEAWVIHGG (SEQ ID NO: 3) of human CD38 (SEQ ID NO: 1).

8. The anti-CD38 antibody, CHOP or combination for use according to embodiment 7, wherein the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

9. The anti-CD38 antibody for use according to any one of embodiments 1, or 4-8, the CHOP for use according to any one of embodiments 2, or 4-8, or the combination for use according to any one of embodiments 3-8, wherein the anti-CD38 antibody:
(i) is of IgG1, IgG2, IgG3 or IgG4 isotype;
(ii) has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%;
(iii) comprises a substitution in the antibody Fc at amino acid position 256, 290, 298, 312, 356, 330, 333, 334, 360, 378 or 430, when residue numbering according to the EU index; and/or
(iv) binds to CD38 with an affinity of $1\times10^{-9}$ or less, $1\times10^{-10}$ or less, $1\times10^{-11}$ or less, or $1\times10^{-12}$ or less.

10. The anti-CD38 antibody for use according to any one of embodiments 1, or 4-9, the CHOP for use according to any one of embodiments 2, or 4-9, or the combination for use according to any one of embodiments 3-9, wherein the anti-CD38 antibody comprises:
(i) the heavy chain complementarity determining regions (HCDR) 1 (HCDR1), 2 (HCDR2) and 3 (HCDR3) sequences of SEQ ID NOs: 6, 7 and 8, respectively;
(ii) the light chain complementarity determining regions (LCDR) 1 (LCDR1), 2 (LCDR2) and 3 (LCDR3) sequences of SEQ ID NOs: 9, 10 and 11, respectively;
(iii) comprises the heavy chain variable region (VH) of SEQ ID NO: 4 and the light chain variable region (VL) of SEQ ID NO: 5;
(iv) comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13; or
(v) comprises the heavy chain of SEQ ID NO: 12 and the light chain of SEQ ID NO: 13.

11. The anti-CD38 antibody for use according to any one of embodiments 1, or 4-10, the CHOP for use according to any one of embodiments 2, or 4-10, or the combination for use according to any one of embodiments 3-10, wherein the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL), specifically wherein the CD38-positive hematological malignancy is DLBCL.

12. The anti-CD38 antibody for use according to any one of embodiments 1, or 4-11, the CHOP for use according to any one of embodiments 2, or 4-11, or the combination for use according to any one of embodiments 3-11, wherein:
(i) the subject is resistant to or has acquired resistance to treatment with at least one chemotherapeutic agent or a combination of at least one chemotherapeutic agent and an anti-CD20 antibody; and/or
(ii) the subject has discontinued treatment with at least one chemotherapeutic agent or a combination of at least one chemotherapeutic agent and an anti-CD20 antibody due to side-effects.

13. The anti-CD38 antibody, CHOP or combination for use according to embodiment 12, wherein the anti-CD20 antibody is rituximab (RITUXAN®), ofatumumab (ARZERRA®), veltuzumab, ocrelizumab, obinutuzumab (GA-101), PRO13192 or ocratuzumab (AME-133v), specifically wherein the anti-CD20 antibody is rituximab.

14. The anti-CD38 antibody, CHOP or combination for use according to embodiment 12 or 13, wherein the at least one chemotherapeutic agent is cyclophosphamide, doxorubicin, vincristine, prednisone, ifosfamide, carboplatin or etoposide, optionally wherein:
(i) the at least one chemotherapeutic agent is a combination of cyclophosphamide, doxorubicin, vincristine and prednisone (CHOP); or
(ii) the at least one chemotherapeutic agent is a combination of ifosfamide, carboplatin and etoposide (ICE).

15. The anti-CD38 antibody for use according to any one of embodiments 1, or 4-14, the CHOP for use according to any one of embodiments 2, or 4-14, or the combination for use according to any one of embodiments 3-14, wherein the anti-CD38 antibody, cyclophosphamide, doxorubicin, vincristine and prednisone are administered simultaneously, sequentially or separately.

16. The anti-CD38 antibody for use according to any one of embodiments 1, or 4-15, the CHOP for use according to any one of embodiments 2, or 4-15, or the combination for use according to any one of embodiments 3-15, wherein the subject is further treated with radiotherapy.

17. The anti-CD38 antibody for use according to any one of embodiments 1, or 4-16, the CHOP for use according to any one of embodiments 2, or 4-16, or the combination for use according to any one of embodiments 3-16, wherein:
(i) the anti-CD38 antibody comprises the heavy chain variable region (VH) of SEQ ID NO: 4 and the light chain variable region (VL) of SEQ ID NO: 5;
(ii) the anti-CD38 antibody is IgG1; and
(iii) wherein the CD38-positive hematological malignancy is DLBCL.

18. The anti-CD38 antibody for use according to any one of embodiments 1, or 4-16, the CHOP for use according to any one of embodiments 2, or 4-16, or the combination for use according to any one of embodiments 3-16, wherein:

(i) the anti-CD38 antibody comprises the heavy chain variable region (VH) of SEQ ID NO: 4 and the light chain variable region (VL) of SEQ ID NO: 5;
(ii) the anti-CD38 antibody is IgG1; and
(iii) wherein the CD38-positive hematological malignancy is Burkitt's lymphoma.

Example 1

Combination Therapy with Daratumumab and CHOP in Patient Derived Non-Hodgkin's Lymphoma (NHL) Models Methods ST1361 is a NHL-DLBCL (diffuse large B-cell lymphoma) PDX (patient derived xenograft) model originating from a fifty-eight year old Hispanic male chemo-naïve prior to metastatic sample collection. The patient had been treated with 8 cycles of R-CHOP prior to the resection, with subsequent treatments with R-ICE and R-GEMOX.

Tumors were implanted in immunocompromised mice between 5-8 weeks of age. When tumors reached approximately 125-250 mm³ (day 0) animals were randomized into treatment and control groups and dosing was initiated on Day 0. Daratumumab was dosed at 20 mg/kg once a week for 3 weeks. CHOP and R-CHOP at the concentrations described below were dosed once on day 0. CHOP (cyclophosphoamide: 30 mg/kg; doxorubicin: 2.5 mg/kg; vincristine: 0.4 mg/kg)-IV DAY 0; prednisone: 0.15 mg/kg DAYS 0-4; R-CHOP: rituximab 20 mg/kg-IP DAY 0. Beginning Day 0, tumor volume was measured twice weekly by digital caliper and data including individual and mean estimated tumor volumes (Mean TV±SEM) recorded for each group. The study was used to measure tumor growth inhibition until the control group was terminated and then continued as a survival study to evaluate the duration of daratumumab efficacy.

For the study, beginning Day 0, tumor dimensions were measured twice weekly by digital caliper and data including individual and mean estimated tumor volumes (mean TV±SEM) recorded for each group. Tumor volume (TV) was calculated using the formula: TV=width²×length×0.52. % tumor growth inhibition (% TGI) values were calculated for each treatment group (T) versus control (C) using initial (i) and final (f) tumor measurements by the formula: % TGI=1−$T_f$−$T_i$/$C_f$−C.

Results

Daratumumab in combination with CHOP or R-CHOP was highly effective in this patient-derived tumor model of DLBCL. On day 31, CHOP regimen by itself slowed the tumor growth by about 27% whereas daratumumab inhibited tumor growth by ~71%. R-CHOP was a more effective therapy with 82% tumor growth inhibition. Combination of daratumumab with CHOP or R-CHOP showed tumor regression and by the end of the study none of the animals had measurable tumors. Beyond day 31, 100% of the animals in

TABLE 1

| Treatment | Mean tumor volume (mm³) ± SEM | % TGI |
| --- | --- | --- |
| Isotype control | 2192 ± 160 | |
| Daratumumab | 744 ± 236 | 71% |
| CHOP | 1634 ± 159 | 27% |
| R-CHOP | 513 ± 104 | 82% |
| Daratumumab/ CHOP | 0 | 107% |

TABLE 1-continued

| Treatment | Mean tumor volume (mm³) ± SEM | % TGI |
| --- | --- | --- |
| Daratumumab/ R-CHOP | 0 | 107% |

% TGI: percent tumor growth inhibition daratumumab+CHOP and daratumumab+R-CHOP survived, the other groups showed loss of animals due to tumor progression. FIG. 1A shows the tumor volume over time for each treatment group, and FIG. 1B shows the median % survival over time. Table 1 shows the % TGI up to day 31 of the study. At day zero, tumor volume for each group was 145-146 mm³. Combination of daratumumab and CHOP resulted in 100% TGI even after 60 days of initiation of the study.

In this study, the efficacy of daratumumab was evaluated in a patient-derived DLBCL model. This patient was treated with R-CHOP and responded to R-CHOP initially but later died due to disease progression. The goal of this study was to determine if addition of daratumumab would offer greater benefit for DLBCL patients. Compared to monotherapy (daratumumab, CHOP or R-CHOP), addition of daratumumab to CHOP or R-CHOP resulted in tumor regression in all animals while the animals in all other groups succumbed to death as a result of disease burden. The combination of daratumumab with CHOP or R-CHOP showed greater than additive effect on tumor growth inhibition.

Example 2

Efficacy of Daratumumab in Combination with CHOP in Burkitt's Lymphoma

As a model for Burkitt's lymphoma, NAMALWA cells were utilized to study the efficacy of daratumumab alone or in combination with CHOP.

Methods

Namalwa cells were maintained in vitro in RPMI 1640 medium supplemented with fetal bovine serum (10% v/v), and L-glutamine (2 mM) at 37° C. in an atmosphere of 5% $CO_2$ in air. The cells were routinely subcultured twice weekly by trypsin-EDTA treatment. The cells growing in an exponential growth phase were harvested and counted for tumor inoculation. The mice were injected with 2×10⁵ Namalwa cells in 0.1 ml of PBS with matrigel (1:1) subcutaneously and the treatments were started when the mean tumor size reached 189 mm³. The date of tumor cell inoculation is denoted as day 0. The major endpoint was to see if the tumor growth can be delayed or tumor-bearing mice can be cured. Tumor sizes were measured twice weekly and % TGI values calculated as described in Example 1.

Results

Animals were divided in four treatment groups and were administered vehicle (isotype control), daratumumab, CHOP or daratumumab in combination with CHOP at dosages as described in Table 2.

TABLE 2

| Groups | n | Treatment | Dose (mg/kg) | Dosing Route | Schedule |
| --- | --- | --- | --- | --- | --- |
| 1 | 10 | Vehicle (IgG) | 10 | i.p | QW × 3 |
| 2 | 10 | Daratumumab | 10 | i.p. | QW × 3 |

TABLE 2-continued

| Groups | n | Treatment | | Dose (mg/kg) | Dosing Route | Schedule |
|---|---|---|---|---|---|---|
| 3 | 10 | CHOP | CTX | 5 | i.v. | QD × 5 |
| | | | Doxorubicin | 0.5 | i.v. | |
| | | | Vincristine | 0.08 | i.v. | |
| | | | Prednisone | 0.03 | p.o. | |
| 4 | 10 | | Daratumumab | 10 | i.p. | QW × 3 |
| | | CHOP | CTX | 5 | i.v. | QD × 5 |
| | | | Doxorubicin | 0.5 | i.v. | |
| | | | Vincristine | 0.08 | i.v. | |
| | | | Prednisone | 0.03 | p.o. | | n, animal number
i.p intraperitoneal injection
i.v. intravenous injection
p.o. oral administration
QD: daily dosing
QW: once a week
CTX: cyclophosphoamide FIG. 2 shows results of the efficacy of daratumumab alone or in combination with CHOP in NAMALWA model of Burkitt's lymphoma. The reduction in tumor sizes (measured as tumor volume) in different treatment groups at different time points after tumor inoculation are shown in FIG. 2. The mean tumor size of the vehicle group (Group 1) reached 4,281 mm$^3$ at day 26 post tumor inoculation. Treatment with daratumumab at 10 mg/kg, CHOP and daratumumab at 10 mg/kg in combination with CHOP produced significant antitumor activity in tumor size at day 26 post tumor inoculation separately. The mean tumor sizes were 3,017 mm$^3$ (T/C value=70.46%, p value<0.001), 3,304 mm$^3$ (T/C value=77.17%, p value=0.003) and 2,303 mm$^3$ (T/C value=53.79%, p value<0.001) at the same time with tumor growth delay of 2, 1 and 4 day(s) respectively at tumor size of 2,303 mm$^3$.

Example 3

Efficacy of Daratumumab in Combination with CHOP in Non-Hodgkin's Lymphoma

SU-DHL-6 cell line based NHL-DLBCL model was utilized to study the efficacy of daratumumab alone or in combination with CHOP.

Methods

The SU-DHL-6 cells were maintained separately in vitro in RPMI1640 medium supplemented with 20% fetal bovine serum (v/v) at 37° C. in an atmosphere of 5% $CO_2$ in air. The cells were routinely subcultured twice weekly. The cells growing in an exponential growth phase were harvested and counted for tumor inoculation. NOD SCID mice were γ-irradiated (200 rads) at 24 h before injection. Each mouse was inoculated subcutaneously at the right flank with SU-DHL-6 tumor cells (5×10$^6$) in 0.1 ml of PBS with matrigel (1:1) for tumor development. The treatments were started when the tumor size reaches approximately 154 mm$^3$. The date of tumor cell inoculation is denoted as day 0. Tumor sizes were measured twice weekly and % TGI values calculated as described in Example 1.

Animals were divided in four treatment groups and were administered vehicle, daratumumab, CHOP or daratumumab in combination with CHOP at dosages as described in Table 3.

The results of tumor sizes in different groups at different time points after tumor inoculation are shown in FIG. 3. The mean tumor size of the vehicle group (Group 1) reached 4,281 mm$^3$ at day 32 post tumor inoculation. Treatment with daratumumab at 10 mg/kg and daratumumab at 10 mg/kg in combination with CHOP produced significant antitumor activity in tumor size at day 32 post tumor inoculation separately. The mean tumor sizes were 1,946 mm$^3$ (T/C value=45.45%, p value=0.006) and 1,611 mm$^3$ (T/C value=37.62%, p value=0.002) at the same time with tumor growth delay of 3 and 3.5 days respectively at tumor size of 1,500 mm$^3$. Treatment with CHOP could decrease tumor size when compared to vehicle group but the decrease didn't reach significant difference.

TABLE 3

| Groups | n[a] | Treatment | | Dose (mg/kg) | Dosing Route[b] | Schedule[c] |
|---|---|---|---|---|---|---|
| 1 | 10 | | Vehicle (IgG) | 10 | i.p. | QW × 4 |
| 2 | 10 | | Daratumumab | 10 | i.p. | QW × 4 |
| 3 | 10 | CHOP | CTX | 5 | i.v. | QD × 5 |
| | | | Doxorubicin | 0.5 | i.v. | |
| | | | Vincristine | 0.08 | i.v. | |
| | | | Prednisone | 0.03 | p.o. | |
| 4 | 10 | | Daratumumab | 10 | i.p. | QW × 4 |
| | | CHOP | CTX | 5 | i.v. | QD × 5 |
| | | | Doxorubicin | 0.5 | i.v. | |
| | | | Vincristine | 0.08 | i.v. | |
| | | | Prednisone | 0.03 | p.o. | | n, animal number
i.p. intraperitoneal injection
i.v. intravenous injection
p.o. oral administration
QD: daily dosing
QW: once a week
CTX: cyclophosphoamide Example 4

Sequential or Simultaneous Therapy with Daratumumab in Combination with CHOP or R-CHOP Provides Efficacy in Patient Derived Non-Hodgkin's Lymphoma (NHL) Models Efficacy of daratumumab alone or in combination with CHOP or R-CHOP was assessed using simultaneous or sequential dosing in the patient derived DLBCL tumor model ST1361 and according to methods described in Example 1.

Animals were divided into treatment groups and dosed as shown in Table 4. Daratumumab and R-CHOP were dosed simultaneously at day 0 or at 7 day interval.

TABLE 4

| Group | n | Treatment | | Dose (mg/kg) | Dosing Route | Schedule |
|---|---|---|---|---|---|---|
| 1 | 10 | | Vehicle (IgG) | 10 | i.p. | QW × 3 |
| 2 | 10 | | Daratumumab | 20 | i.p. | QW × 3 |
| | | CHOP | CTX | 5 | i.v. | D0 |
| | | | Doxorubicin | 0.5 | i.v. | D0 |

TABLE 4-continued

| Group | n | Treatment | | Dose (mg/kg) | Dosing Route | Schedule |
|---|---|---|---|---|---|---|
| | | | Vincristine | 0.08 | i.v. | D0 |
| | | | Prednisone | 0.03 | p.o. | D0-4 |
| 3 | 10 | | Daratumumab | 20 | i.p. | QW × 3 |
| | | R-CHOP | Rituximab | 20 | i.p. | QW × 3 |
| | | | CTX | 5 | i.v. | D0 |
| | | | Doxorubicin | 0.5 | i.v. | D0 |
| | | | Vincristine | 0.08 | i.v. | D0 |
| | | | Prednisone | 0.03 | p.o. | D0-4 |
| 4 | 10 | | Daratumumab | 20 | i.p. | D7 |
| | | R-CHOP | Rituximab | 20 | i.p. | D0 |
| | | | CTX | 5 | i.v. | D0 |
| | | | Doxorubicin | 0.5 | i.v. | D0 |
| | | | Vincristine | 0.08 | i.v. | D0 |
| | | | Prednisone | 0.03 | p.o. | D0-4 |
| 5 | 10 | Daratumumab | Daratumumab | 20 | i.p. | D0 |
| | | R-CHOP | Rituximab | 20 | i.p. | D7 |
| | | | CTX | 5 | i.v. | D0 |
| | | | Doxorubicin | 0.5 | i.v. | D0 |
| | | | Vincristine | 0.08 | i.v. | D0 |
| | | | Prednisone | 0.03 | p.o. | D0-4 | n, animal number
i.p intraperitoneal injection
i.v. intravenous injection
p.o. oral administration
QD: daily dosing
QW: once a week dosing
D0 = day 0 dosing
D0-4 = dosing once a day at days d0-d4

Results

FIG. 4 shows the results of tumor growth curves in response treatment up to 45 days of the study. Tumors in the vehicle control group reached a mean tumor volume of 2134 mm$^3$ by day 17. Tumors in the daratumumab+CHOP group regressed to a mean tumor volume of 96 mm$^3$ by day 45. Tumors in animals treated with daratumumab and R-CHOP simultaneously on day 0 (group 4), completely regressed by day 45. Tumors in animals treated with R-CHOP on day 0, followed by daratumumab on day 7 (group 5) showed mean tumor volume of 998 mm$^3$. Tumors that were treated with daratumumab on day 0, followed by R-CHOP on day 7 (group 6) showed mean tumor volume of 633 mm$^3$. The study was continued to up to 101 days Animals treated with daratumumab and R-CHOP simultaneously on day 0 (group 4), completely regressed by day 101 also.

---

The invention claimed is:

1. A method of treating a subject having a CD38-positive hematological malignancy, comprising administering to the subject in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity and comprises heavy chain complementarity determining region (HCDR) 1 (HCDR1), 2 (HCDR2) and 3 (HCDR3) sequences of SEQ ID NOs: 6, 7 and 8, respectively, and light chain complementarity determining region (LCDR) 1 (LCDR1), 2 (LCDR2) and 3 (LCDR3) sequences of SEQ ID NOs: 9, 10 and 11, respectively, wherein the subject is resistant to or has acquired resistance to treatment with at least one chemotherapeutic agent.

2. The method of claim 1, wherein the anti-CD38 antibody induces killing of the CD38-expressing cells by ADCC or CDC in vitro.

3. The method of claim 2, wherein the anti-CD38 antibody is of IgG1, IgG2, IgG3 or IgG4 isotype.

4. The method of claim 3, wherein the anti-CD38 antibody has a biantennary glycan structure with fucose content of about 50%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

5. The method of claim 3, wherein the anti-CD38 antibody comprises a substitution in the antibody Fc at amino acid position 256, 290, 298, 312, 356, 330, 333, 334, 360, 378 or 430, wherein residue numbering is according to the EU index.

6. The method of claim 1, wherein the anti-CD38 antibody comprises a heavy chain variable region (VH) of SEQ ID NO: 4 and a light chain variable region (VL) of SEQ ID NO: 5.

7. The method of claim 6, wherein the anti-CD38 antibody comprises a heavy chain of SEQ ID NO: 12 and a light chain of SEQ ID NO: 13.

8. The method of claim 1, wherein the CD38-positive hematological malignancy is multiple myeloma, acute lymphoblastic leukemia (ALL), non-Hodgkin's lymphoma (NHL), diffuse large B-cell lymphoma (DLBCL), Burkitt's lymphoma (BL), follicular lymphoma (FL) or mantle-cell lymphoma (MCL).

9. The method of claim 8, wherein the CD38-positive hematological malignancy is DLBCL.

10. The method of claim 8, wherein the subject is resistant to or has acquired resistance to treatment with a combination of at least one chemotherapeutic agent and an anti-CD20 antibody.

11. The method of claim 8, wherein the subject has discontinued treatment with at least one chemotherapeutic agent or a combination of at least one chemotherapeutic agent and an anti-CD20 antibody due to side effects.

12. The method of claim 10 or 11, wherein the anti-CD20 antibody is rituximab (RITUXAN®), ofatumumab (ARZERRA®), veltuzumab, ocrelizumab, obinutuzumab (GA-101), PRO13192 or ocratuzumab (AME-133v).

13. The method of claim 12, wherein the anti-CD20 antibody is rituximab.

14. The method of claim 10 or 11, wherein the at least one chemotherapeutic agent is cyclophosphamide, doxorubicin, vincristine, prednisone, ifosfamide, carboplatin or etoposide.

15. The method of claim 14, wherein the at least one chemotherapeutic agent is a combination of cyclophosphamide, doxorubicin, vincristine and prednisone (CHOP).

16. The method of claim 14, wherein the at least one chemotherapeutic agent is a combination of ifosfamide, carboplatin and etoposide (ICE).

17. The method of claim 1, wherein the anti-CD38 antibody, cyclophosphamide, doxorubicin, vincristine and prednisone are administered simultaneously, sequentially or separately.

18. The method of claim 1, wherein the patient is further treated with radiotherapy.

* * * * *